US012140585B2

United States Patent
Koseoglu et al.

(10) Patent No.: US 12,140,585 B2
(45) Date of Patent: Nov. 12, 2024

(54) ESTIMATING MOLECULAR WEIGHT OF HYDROCARBONS

(71) Applicant: Saudi Arabian Oil Company, Dhahran (SA)

(72) Inventors: Omer Refa Koseoglu, Dhahran (SA); Saroj Kumar Panda, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 527 days.

(21) Appl. No.: 17/376,540

(22) Filed: Jul. 15, 2021

(65) Prior Publication Data

US 2023/0026355 A1   Jan. 26, 2023

(51) Int. Cl.
| | |
|---|---|
| *G01N 33/28* | (2006.01) |
| *G01N 21/359* | (2014.01) |
| *G16C 20/30* | (2019.01) |
| *B01J 20/291* | (2006.01) |
| *G01N 9/36* | (2006.01) |
| *G01N 21/31* | (2006.01) |

(52) U.S. Cl.
CPC ....... *G01N 33/2823* (2013.01); *G01N 21/359* (2013.01); *G16C 20/30* (2019.02); *B01J 20/291* (2013.01); *G01N 9/36* (2013.01); *G01N 2021/3155* (2013.01)

(58) Field of Classification Search
CPC .... G01N 21/359; G01N 33/2823; G01N 9/36; G16C 20/30
See application file for complete search history.

(56) References Cited

U.S. PATENT DOCUMENTS

| | | |
|---|---|---|
| 6,633,043 B2 | 10/2003 | Hegazi et al. |
| 7,091,719 B2 | 8/2006 | Freedman |
| 8,093,056 B2 | 1/2012 | Ganesan |
| 9,285,307 B2 | 3/2016 | Koseoglu et al. |
| 9,778,240 B2 | 10/2017 | Koseoglu et al. |
| 9,816,919 B2 | 11/2017 | Koseoglu et al. |
| 9,934,367 B2 | 4/2018 | Chen et al. |
| 10,031,121 B2 | 7/2018 | Koseoglu et al. |
| 10,048,194 B2 | 8/2018 | Koseoglu et al. |
| 10,288,755 B2 | 5/2019 | Cordery |
| 10,345,285 B2 | 7/2019 | Koseoglu et al. |
| 10,351,763 B2 | 7/2019 | Almohsin et al. |

(Continued)

FOREIGN PATENT DOCUMENTS

| | | |
|---|---|---|
| CA | 2740845 | 2/2017 |
| WO | WO 2009051742 | 4/2009 |

OTHER PUBLICATIONS

U.S. Appl. No. 62/449,191, Al Enezi, filed Jan. 23, 2017.

(Continued)

*Primary Examiner* — Nathaniel J Kolb
(74) *Attorney, Agent, or Firm* — Fish & Richardson P.C.

(57) ABSTRACT

A method and a system for predicting a molecular weight of a hydrocarbon fluid are provided. An exemplary method includes measuring a density of the hydrocarbon fluid, obtaining an alternative measurement of a physical property of the hydrocarbon fluid, calculating an index value for the hydrocarbon fluid from the alternative measurement, and calculating a predicted molecular weight using an equation that combines the density with the index value. The predicted molecular weight is provided as an output.

7 Claims, 3 Drawing Sheets

(56) References Cited

U.S. PATENT DOCUMENTS

| | | | |
|---|---|---|---|
| 10,401,344 | B2 | 9/2019 | Koseoglu et al. |
| 10,527,546 | B2 | 1/2020 | Koseoglu et al. |
| 10,557,330 | B2 | 2/2020 | Oliveira et al. |
| 10,571,452 | B2 | 2/2020 | Koseoglu et al. |
| 10,627,345 | B2 | 4/2020 | Koseoglu et al. |
| 10,648,891 | B2 | 5/2020 | He et al. |
| 10,655,443 | B2 | 5/2020 | Gomaa et al. |
| 10,677,718 | B2 | 6/2020 | Koseoglu et al. |
| 10,684,239 | B2 | 6/2020 | Koseoglu et al. |
| 10,725,013 | B2 | 7/2020 | Koseoglu et al. |
| 10,794,821 | B2 | 10/2020 | Koseoglu et al. |
| 2015/0006084 | A1* | 1/2015 | Zuo ............. E21B 49/088 702/13 |
| 2019/0186818 | A1 | 6/2019 | Noureldin |

OTHER PUBLICATIONS

ASTM D2502-14 (2019), Standard Test Method for Estimation of Mean Relative Molecular Mass of Petroleum Oils from Viscosity Measurements.

ASTM D2503-92 (2016), Standard Test Method for Relative Molecular Mass (Molecular Weight) of Hydrocarbons by Thermoelectric Measurement of Vapor Pressure.

ASTM D2878-10 (2016), Standard Test Method for Estimating Apparent Vapor Pressures and Molecular Weights of Lubricating Oils.

ASTM D2887 (2019), Standard Test Method for Boiling Range Distribution of Petroleum Fractions by Gas Chromatography.

ASTM D2892-20 (2020), Standard Test Method for Distillation of Crude Petroleum (15-Theoretical Plate Column) Jun. 10, 2020.

ASTM D4052-18a (2018), Standard Test Method for Density, Relative Density, and API Gravity of Liquids by Digital Density Meter.

ASTM D6474-20 (2020), Standard Test Method for Determining Molecular Weight Distribution and Molecular Weight Averages of Polyolefins by High Temperature Gel Permeation Chromatography.

ASTM D6579-11 (2020), Standard Practice for Molecular Weight Averages and Molecular Weight Distribution of Hydrocarbon, Rosin and Terpene Resins by Size-Exclusion Chromatography.

ASTM D7134-05 (2012), Standard Test Method for Molecular Mass Averages and Molecular Mass Distribution of Atactic Polystyrene by Matrix Assisted Laser Desorption/Ionization (MALDI)—Time of Flight (TOF) Mass Spectrometry (MS).

* cited by examiner

ESTIMATING MOLECULAR WEIGHT OF HYDROCARBONS

TECHNICAL FIELD

The present disclosure is directed to the use of analysis techniques to predict molecular weight of a crude oil using a density measurement combined with an index value from a second, or alternative, measurement, such as spectroscopic, chromatographic, or thermographic analysis.

BACKGROUND

Crude oil originates from the decomposition and transformation of living organisms, mainly marine, and land plants that became buried under successive layers of mud and silt between about 15 and about 500 million years ago. As a result, crude oil is a complex mixture that may include thousands of different hydrocarbons. Depending on the source, the oil may include various proportions of straight and branched-chain paraffins, cycloparaffins, naphthenic hydrocarbons, aromatic hydrocarbons, and polynuclear aromatic hydrocarbons. The hydrocarbons can be gaseous, liquid, or solid under normal conditions of temperature and pressure, depending on the number and arrangement of carbon atoms in the molecules.

Crude oils vary widely in their physical and chemical properties from one geographical region to another and from field to field. Crude oils are usually classified into three groups according to the nature of the hydrocarbons they include: paraffinic, naphthenic, asphaltic, and their mixtures. The classification is based on the different proportions of the various molecular types and sizes. For example, one type of crude oil can contain mostly paraffins, while another type is mostly made up of naphthenes. Further, the crude oil may contain dissolved gases or a large quantity of lighter hydrocarbons, lowering the viscosity. Other crude oils may include little or no dissolved gas or light hydrocarbons, and may be highly viscous. Crude oils can also include heteroatom compounds containing sulfur, nitrogen, nickel, vanadium and other elements in quantities, which affect the processing of the crude oil fractions. Light crude oils or condensates can contain sulfur in concentrations as low as about 0.01 wt. %. In contrast, heavy crude oils can contain as much as about 5 wt. % to about 6 wt. %. Similarly, the nitrogen content of crude oils can range from about 0.001 wt. % to about 1.0 wt. %.

The composition of the crude oil affects the nature of the products that can be manufactured from it and their suitability for applications. For example, a naphthenic crude oil will be more suitable for the production of asphaltic bitumen, while a paraffinic crude oil is more suited for manufacturing waxes. Naphthenic and paraffinic crude oils may be used for manufacturing lubricating oils with viscosities that are sensitive to temperature. It can be noted that modern refining methods allow flexibility in the use of various crude oils to produce many desired types of products.

SUMMARY

An embodiment described in examples herein provides a method for predicting a molecular weight of a hydrocarbon fluid. The method includes measuring a density of the hydrocarbon fluid, obtaining an alternative measurement of a physical property of the hydrocarbon fluid, calculating an index value for the hydrocarbon fluid from the alternative measurement, and calculating a predicted molecular weight using an equation that combines the density with the index value. The predicted molecular weight is provided as an output.

Another embodiment described in examples herein provides a system for predicting a molecular weight of a hydrocarbon fluid. The system includes a processor and a data store, the data store includes code that, when executed, directs the processor to collect a density measurement, collect data from an alternative measurement, calculate an index value from the data from the alternative measurement, calculate a predicted molecular weight from the density measurement and the index value, and output the predicted molecular weight.

DETAILED DESCRIPTION

Molecular weight of hydrocarbons can be determined using available standard analytic methods. These methods include, for example, standard tests such as: ASTM D2502-14(2019)e1 Standard Test Method for Estimation of Mean Relative Molecular Mass of Petroleum Oils from Viscosity Measurements, May 7, 2020; ASTM D2503-92(2016) Standard Test Method for Relative Molecular Mass (Molecular Weight) of Hydrocarbons by Thermoelectric Measurement of Vapor Pressure, Oct. 1, 2016; ASTM D2878-10(2016) Standard Test Method for Estimating Apparent Vapor Pressures and Molecular Weights of Lubricating Oils, Jan. 1, 2016; ASTM D6474-20 Standard Test Method for Determining Molecular Weight Distribution and Molecular Weight Averages of Polyolefins by High Temperature Gel Permeation Chromatography, May 7, 2020; and ASTM D6579-11(2020) Standard Practice for Molecular Weight Averages and Molecular Weight Distribution of Hydrocarbon, Rosin and Terpene Resins by Size-Exclusion Chromatography, Jul. 8, 2020; among others.

However, these methods may require equipment that may not be available at a field or laboratory site. Further, the tests take a long time to determine molecular weight. Accordingly, performing assays on hydrocarbons from a well, for example, to make decisions during drilling, completion, and processing, may be delayed, substantially increasing costs.

Embodiments described herein provide a method and a system for estimating molecular weight of a hydrocarbon fraction from the density of the hydrocarbon fraction in combination with an alternate measurement including, for example, a spectroscopic, chromatographic, or thermogravimetric measurement. In the techniques, a density of a crude oil sample is measured. An index value is calculated from data from an alternate measurement of the oil sample. The alternative measurements can include any number of techniques for measuring properties of the crude oil including, for example, near infrared spectroscopy, Fourier transform infrared spectroscopy, ultra-violet visible spectroscopy, nuclear magnetic spectroscopy, gas or liquid chromatography, or thermogravimetric analysis, among others. Combinations of these techniques may also be used to develop correlation functions with density for the prediction of molecular weight.

Figure 1:
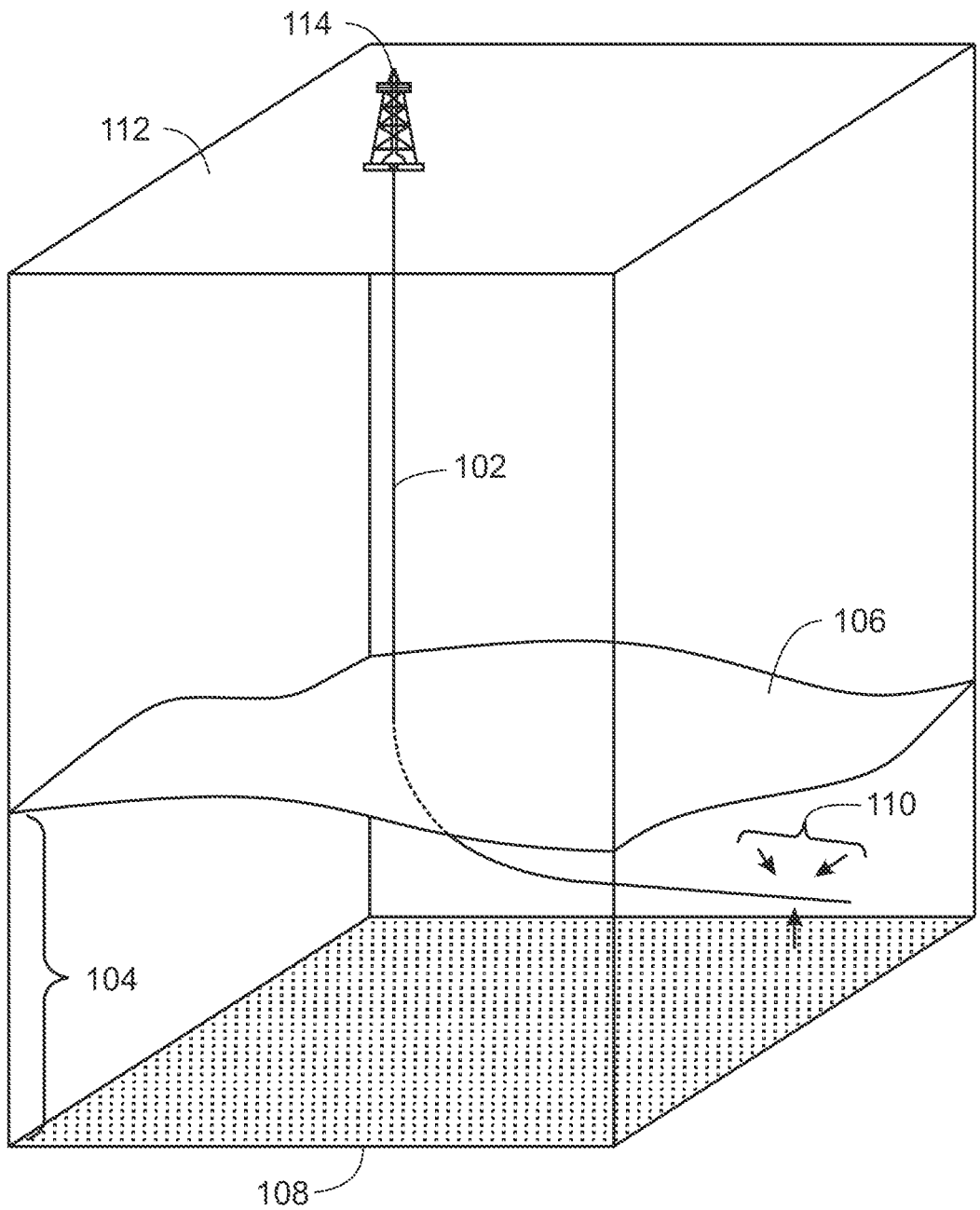
FIG. 1 is a schematic drawing of a wellbore drilled to a hydrocarbon reservoir layer.

FIG. 1 is a schematic drawing 100 of a wellbore 102 drilled to a hydrocarbon reservoir layer 104. In many examples, the hydrocarbon reservoir layer 104 is generally located between a layer of cap rock 106 and a lower layer, which may include a water layer 108. The crude oil 110 enters the wellbore 102 and is transported to the surface 112, for example, for sampling at a drilling rig 114. In this example, the wellbore 102 is directionally drilled to reach the crude oil 110. Samples of the crude oil 110 may be used to determine the properties, which may be useful for modifying drilling direction, determining completion strategy, modifying production strategy, determining shipping strategy, or optimizing product mix for products formed from the crude oil. The technique depends on the quality of the oil to be processed. The quality of the oil will impact the shipping, pipelining, refinery processing, and the processability to final products. A technique for the fast determination of these properties A crude oil assay is a traditional method of determining the nature of crude oils for benchmarking purposes, for example, against each other or reference crude oils, such as Brent crude oil, West Texas intermediate crude oil, or Arab light crude oil. Crude oils are subjected to true boiling point (TBP) distillations and fractionations to provide different boiling point fractions. The crude oil distillations are carried out using the American Standard Testing Association (ASTM) Method D2892 (ASTM D2892-20 Standard Test Method for Distillation of Crude Petroleum (15-Theoretical Plate Column) Jun. 10, 2020). The common fractions and their nominal boiling points are given in Table 1.

TABLE 1

Common fractions and their nominal boiling points

| Fraction | Boiling Point, ° C. |
| --- | --- |
| Methane | −161.5 |
| Ethane | −88.6 |
| Propane | −42.1 |
| Butanes | −6.0 |
| Light Naphtha | 36-90 |
| Mid Naphtha | 90-160 |
| Heavy Naphtha | 160-205 |
| Light gas Oil | 205-260 |
| Mid Gas Oil | 260-315 |
| Heavy gas Oil | 315-370 |
| Light Vacuum Gas Oil | 370-430 |
| Mid Vacuum Gas Oil | 430-480 |
| Heavy vacuum gas oil | 480-565 |
| Vacuum Residue | 565+ |

The yields, composition, physical, and properties of these crude oil fractions, where applicable, are determined during the crude assay work-up calculations. Typical compositional and property information obtained from a crude oil assay is given in Table 2.

TABLE 2

Information obtained from a crude oil assay

| Property | Unit | Property Type | Fraction |
| --- | --- | --- | --- |
| Yield Weight and Volume % | W % | Yield | All |
| API Gravity | ° | Physical | All |

TABLE 2-continued

Information obtained from a crude oil assay

| Property | Unit | Property Type | Fraction |
| --- | --- | --- | --- |
| Viscosity Kinematic @ 38° C. | ° | Physical | Fraction boiling >250° C. |
| Refractive Index @ 20° C. | | Physical | Fraction boiling <400° C. |
| Sulfur | W % | Composition | All |
| Mercaptan Sulfur, W % | W % | Composition | Fraction boiling <250° C. |
| Nickel | ppmw | Composition | Fraction boiling >400° C. |
| Nitrogen | ppmw | Composition | All |
| Flash Point, COC | ° C. | Indicative | All |
| Cloud Point | ° C. | Indicative | Fraction boiling >250° C. |
| Pour Point, (Upper) | ° C. | Indicative | Fraction boiling >250° C. |
| Freezing Point | ° C. | Indicative | Fraction boiling >250° C. |
| Microcarbon Residue | W % | Indicative | Fraction boiling >300° C. |
| Smoke Point, mm | mm | Indicative | Fraction boiling between 150-250 |
| Octane Number | Unitless | Indicative | Fraction boiling <250° C. |
| Cetane Index | Unitless | Indicative | Fraction boiling between 150-400 |
| Aniline Point | ° C. | Indicative | Fraction boiling <520° C. |

Due to the number of distillation cuts and the number of analyses involved, the crude oil assay work-up is costly and time consuming, and, thus, a faster analysis is useful for making early decisions for shipping, purchasing, and processing. In a typical refinery, crude oil is first fractionated in the atmospheric distillation column to separate sour gas and light hydrocarbons, including methane, ethane, propane, butanes and hydrogen sulfide, naphtha (at about 36° C. to 180° C.), kerosene (at about 180° C. to about 240° C.), gas oil (at about 240° C. to about 370° C.) and atmospheric residue (greater than about 370° C.). The atmospheric residue from the atmospheric distillation column is either used as fuel oil or sent to a vacuum distillation unit, depending on the configuration of the refinery. The principal products obtained from vacuum distillation are vacuum gas oil, comprising hydrocarbons boiling in the range of about 370° C. to about 520° C., and vacuum residue, comprising hydrocarbons boiling above about 520° C. The crude assay data help refiners to understand the general composition of the crude oil fractions and properties so that the fractions can be processed most efficiently and effectively in an appropriate refining unit.

Gel permeation chromatography (GPC) is a technique commonly used to separate compounds based on the size in solution. Recently, a method using GPC has been used to determine the weight average molecular weights of crude oils. The weight average molecular weight is calculated by:

$$Mw = \frac{\sum_{i=1}^{N} h^i M^i}{\sum_{i=1}^{N} h^i}$$

In this equation, $h_i$ is the GPC curve height at the $i^{th}$ volume increment, and $M_i$ is the molar mass of the species eluted at the $i^{th}$ retention volume. The equation assumes that $h_i$ is proportional to analyte concentration, and M is sampled in equal volume increments. Also, molar absorptivity for all eluted species is assumed to be same. The molar mass for each $i^{th}$ volume is calculated relative to polystyrene standards used for calibration of the column.

Figure 2:
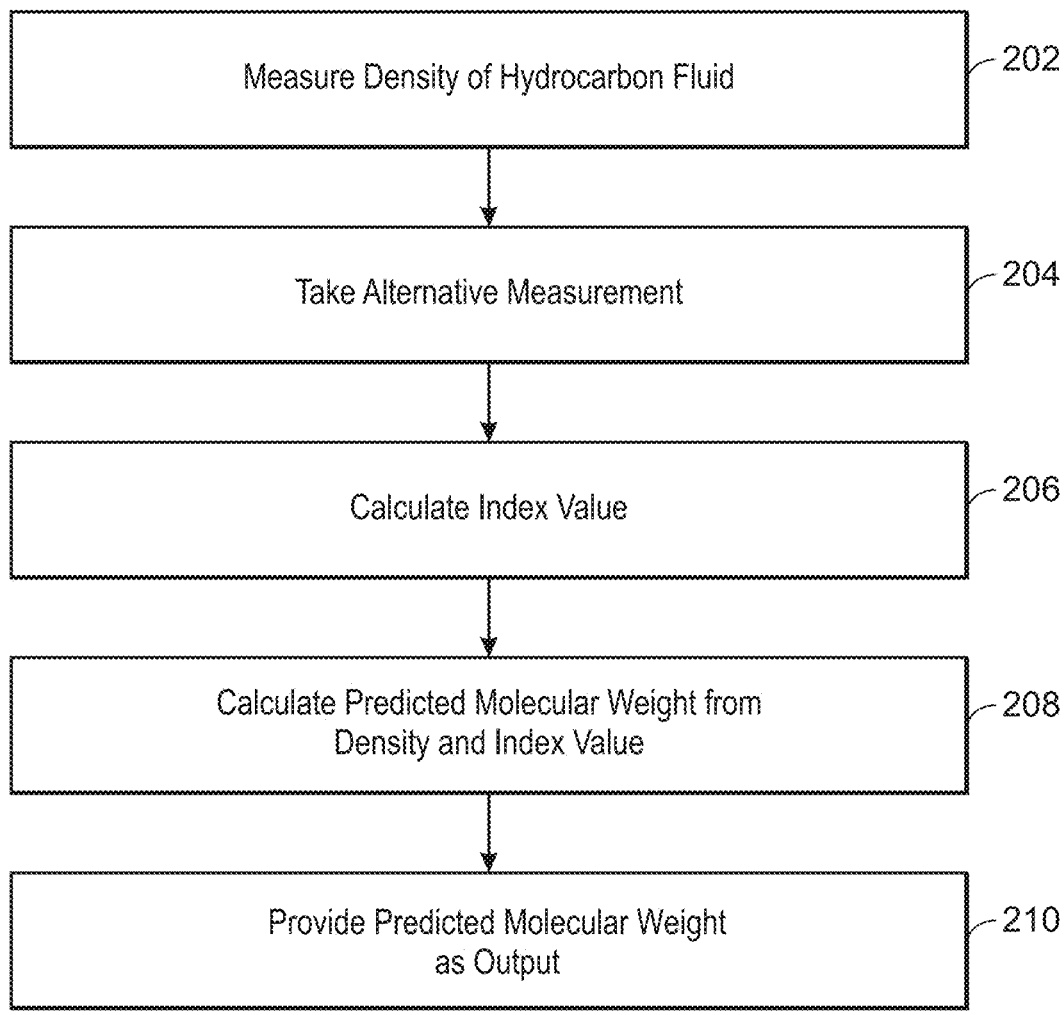
FIG. 2 is a process flow diagram of a method for predicting a molecular weight of a hydrocarbon fluid.

FIG. 2 is a process flow diagram of a method 200 for predicting a molecular weight of a hydrocarbon fluid. The method 200 starts at block 202 with the measurement of the density of the hydrocarbon fluid. In some embodiments, this is performed using the technique of ASTM D 4052, for example, at a standard temperature of 15° C. The temperature may be adjusted for different samples, so long as the standards used for the statistical analysis have been run at the same temperatures.

At block 204, an alternative measurement is taken. In various embodiments, the alternative measurement is a near infrared (NIR) spectrum, a Fourier transform infrared spectrum, an ultraviolet/visible (UV/VIS) spectrum, a simulated distribution (SIMDIST) analysis, or a thermogravimetric (TGA) analysis, among others described herein. The procedures for collecting the alternative measurements are described with respect to the examples.

At block 206, the data from the alternative measurement of each crude oil is used to calculate an index value descriptive of each crude oil. In an embodiment, the determination of the index value is performed from a NIR spectrum using the following equation:

$$NIRA = \sum_{i=4,000}^{12,821} (Absorbance_{(i)})/10,000,$$

wherein absorbance is the absorbance value of the crude oil solution at each wavenumber (cm$^{-1}$) between 4,000 cm$^{-1}$ to 12,821 cm$^{-1}$.

In an embodiment, the determination of the index value is performed from an FTIR spectrum using the following equation:

$$FTIRI = maxtrans_{desired\ crude} - maxtrans_{lowest\ value},$$

wherein the maximum transmittances (maxtrans) are determined for each of a number of crude oils under investigation.

In an embodiment, the determination of the index value is performed from an UV/VIS spectrum using the following equation:

$$CUVISI = \sum_{220}^{400} 2(Absorbance/x),$$

wherein Absorbance is the absorbance value of the crude oil solution at each specific wavelength over the range of 220 nm to 400 nm at 2 nm intervals, and x is the weight of the sample used.

In an embodiment, the determination of the index value is performed from an SIMDIST data set using the following equation:

$$WABT = \frac{[T10*10 + T30*30 + T50*50 + T70*70 + T90*90]}{[10 + 30 + 50 + 70 + 90]}.$$

WABP stands for weighted average boiling point. Simulated distillation (SD) is a technique which separates individual hydrocarbon components in the order of their boiling points, and is used to simulate laboratory-scale physical distillation procedures. The separation can be accomplished with a gas chromatograph equipped with a chromatography column coated with a nonpolar (hydrocarbon-like) stationary phase, an oven and injector which can be temperature programmed. A flame ionization detector (FID) is used for detection and measurement of the hydrocarbon analytes. The SD analysis result provides a quantitative percent mass yield as a function of boiling point of the hydrocarbon components of the sample being analyzed. The chromatographic elution times of the hydrocarbon components are calibrated to the atmospheric equivalent boiling point (AEBP) of the individual n-alkane as described in a method from the ASTM by using n-alkane (n-paraffin) reference material. In the SD method ASTM D2887, the n-alkane calibration reference covers the boiling range 55-538° C. (100-1000.degree. F.) which covers the n-alkanes with a chain length of about C5-C44. T10 is the boiling temperature of oil determined when 10 wt. % or vol. % of the fraction recovered during the distillation. For example, below is a distillation data for a hydrocarbon stream. When the sample is distilled, the boiling point of sample is determined to be 149° C. when 10 wt. % of sample is recovered. T10 is 149° C. Similarly, T30 is 230° C.

In an embodiment, the determination of the index value is performed from a thermogravimetric analysis TGA data set using the following equation:

$$TGAI = \frac{\begin{array}{c}[5*T_5 + 10*T_{10} + 20*T_{20} + 30*T_{30} + \\ 40*T_{40} + 50*T_{50} + 60*T_{60} + \\ 70*T_{70} + 80*T_{80} + 90*T_{90} + 95*T_{95}]\end{array}}{[5 + 10 + 20 + 30 + 40 + 50 + 60 + 70 + 80 + 90 + 95]},$$

wherein $T_n$ is the temperature at each individual mass percentage. Thermogravimetric analysis measures a sample's weight as it is heated or cooled in a controlled atmosphere to provide volatility information of the oil sample under investigation. TGA requires a high degree of precision in the mass change and temperature.

A thermogravimetric analyzer is used, comprising a furnace that contains a sample pan that is supported by a precision balance. A sample purge gas controls the sample environment. This gas may be inert or a reactive gas that flows over the sample and exits through an exhaust. Similar equipment can be used. The temperature range for the TGA analyzer can extend from ambient temperature, e.g., about 20° C., to an upper limit of up to about 1000° C. Heating can be at a rate in the range of about 0.1-100° C./minute.

At block 208, the index value and density of the crude oil are used to estimate a molecular weight for the crude oil. In some embodiments, this is performed using the equation:

Molecular Weight=Constant+$X_1$*DEN+$X_2$*DEN$^2$+ $X_3$*DEN$^3$+$X_4$*Index+$X_5$*Index$^2$+$X_6$*Index$^3$+ $X_7$*DEN*Index, wherein $X_1$, $X_2$, $X_3$, $X_4$, $X_5$, $X_6$, and $X_7$ are coefficients determined by a multiple regression analysis, DEN is the density value, and Index is the index value. Other equations may be used, depending on the statistical derivation of the model. At block 210, the estimated molecular weight of the crude oil is provided as an output, for example, by being displayed on a screen.

Figure 3:
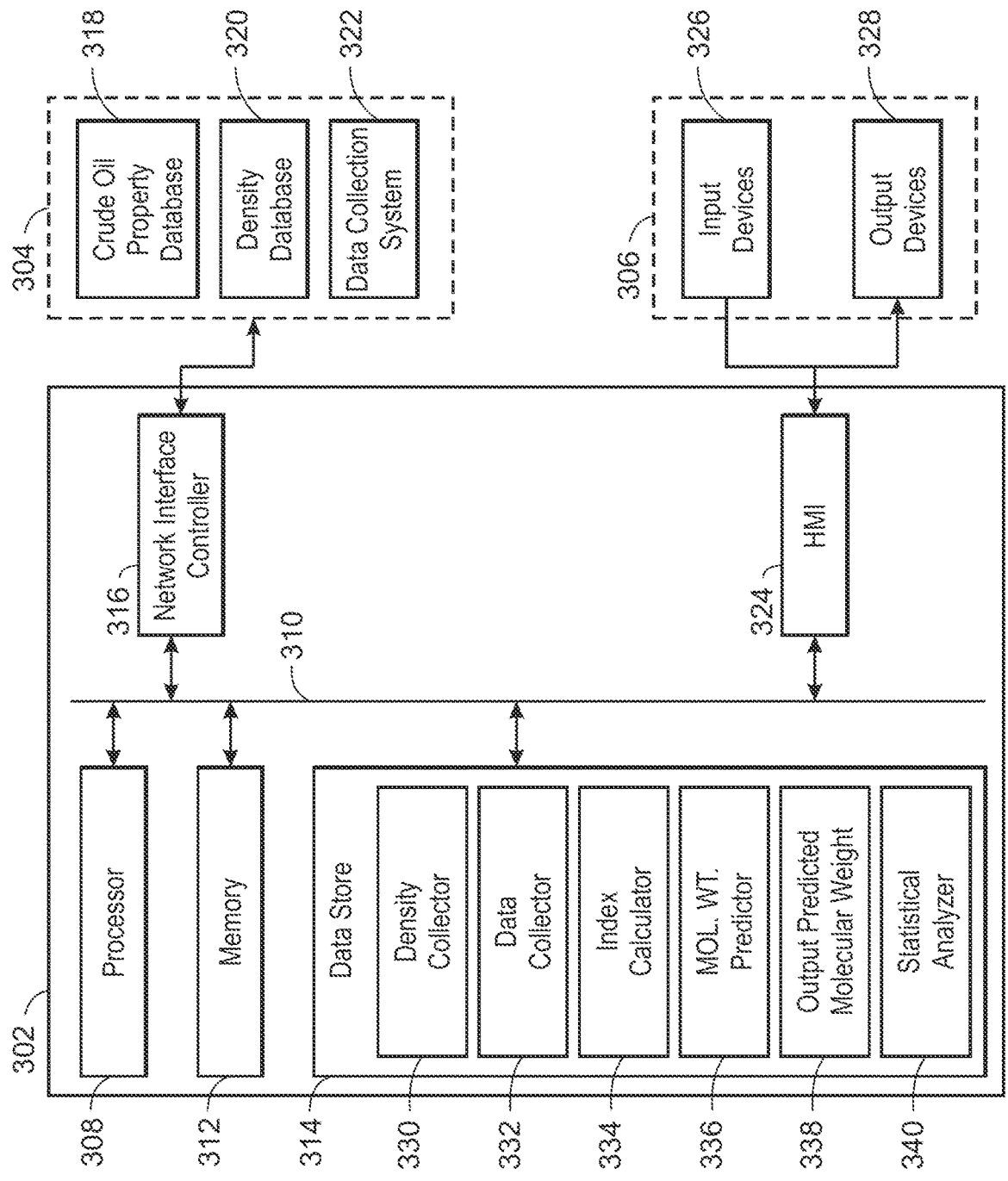
FIG. 3 is a block diagram of a computational system that can implement a method for predicting a molecular weight of a hydrocarbon from a density and an alternate measurement.

FIG. 3 is a block diagram of a computational system 300 that can implement a method for predicting a molecular weight of a hydrocarbon from a density and an alternate measurement. The computational system 300 includes a computing unit 302, an external network 304, and I/O devices 306. In some embodiments, the computing unit 302 is a computer, a workstation, or a laptop, among others. In other embodiments, the computing unit 302 is a virtual machine running on a processor in a cloud computing system, on a virtual processor in a cloud server, or using other real or virtual processors.

The computing unit 302 includes a processor 308. The processor 308 may be a microprocessor, a multi-core processor, a multithreaded processor, an ultra-low-voltage processor, an embedded processor, or a virtual processor. In some embodiments, the processor 308 may be part of a system-on-a-chip (SoC) in which the processor 308 and the other components of the computing unit 302 are formed into a single integrated electronics package, for example, integrated into a data collection system. In various embodiments, the processor 308 may include processors from Intel® Corporation of Santa Clara, California, from Advanced Micro Devices, Inc. (AMD) of Sunnyvale, California, or from ARM Holdings, LTD., Of Cambridge, England. Any number of other processors from other suppliers may also be used.

The processor 308 may communicate with other components of the computing unit 302 over a bus 310. The bus 310 may include any number of technologies, such as industry standard architecture (ISA), extended ISA (EISA), peripheral component interconnect (PCI), peripheral component interconnect extended (PCIx), PCI express (PCIe), or any number of other technologies. The bus 310 may be a proprietary bus, for example, used in an SoC based system. Other bus technologies may be used, in addition to, or instead of, the technologies above.

The bus 310 may couple the processor 308 to a memory 312. The memory 312 include any number of volatile and nonvolatile memory devices, such as volatile random-access memory (RAM), static random-access memory (SRAM), flash memory, and the like. The memory 312 holds currently operating programs, systems, and results.

The bus 310 may couple the processor 308 to a data store 314. The data store 314 is used for the persistent storage of information, such as data, applications, operating systems, and so forth. The data store 314 may be a nonvolatile RAM, a solid-state disk drive, or a flash drive, among others. In some embodiments, the data store 314 will include a hard disk drive, such as a micro hard disk drive, a regular hard disk drive, or an array of hard disk drives, for example, associated with a network or cloud server.

The bus 310 couples the processor 308 to a network interface controller 316. In some embodiments, the network interface controller 316 connects the computing unit 302 to data sources and sinks located in the external network 304, for example, through an Ethernet connection. The external network 304 may be a local network, a corporate intranet, or the Internet, among others. In various embodiments, the data sources and sinks include a crude oil property database 318 that provides spectral measurements, TGA measurements, or SIMDIST measurements for crude oil samples. The crude oil property database 318 may include information provided by outside sources, such as academic, oil producing or refining companies and private research organizations, as well as information specifically measured for the techniques described herein.

A density database 320, may provide density measurements for the crude oil samples. In some embodiments, this is combined with the crude oil property database 318. A data collection system 322 may be included in the external network 304 to directly provide data from alternate measurements. In various embodiments, the data collection system 322 includes an NIR spectrophotometer, an FTIR spectrophotometer, a UV/VIS spectrophotometer, a gas chromatography unit, a liquid chromatography unit configured to run simulated distillations, or a thermogravimetric analyzer, or any number of these units. In some embodiments, the computational system 300 may be incorporated into a measurement system. For example, in an embodiment, a field NIR incorporates the molecular weight prediction system.

The bus 310 couples the processor 308 to a human machine interface (HMI) 324. The HMI 324 couples the computing unit 302 to the I/O devices 306. The I/O devices 306 include input devices 326, such as keyboards, pointing devices, and microphones, among others. The I/O devices 306 include output devices 328, such as monitors, printers, plotters, and speakers, among others.

The data store 314 includes blocks of stored instructions that, when executed, direct the processor 308 to implement the functions of the computational system 300. The data store 314 includes a block 330 of instructions to direct the processor 308 to collect a density measurement. In various embodiments, this is performed by prompting a user to enter the values through the I/O devices 306. In some embodiments, the block 330 provides instructions on how to measure the density, or operates an automated unit that performs the density measurement.

The data store 314 includes a block 332 of instructions that directs the processor 308 to collect data from an alternative measurement. In various embodiments, this is performed by accessing the data from an instrument, such as a NIR spectrophotometer, an FTIR spectrophotometer, a UV/VIS spectrophotometer, a gas chromatograph running a SIMDIST analysis, or a TGA, among others. In some embodiments, the block 332 of instructions directs the processor 308 to operate the instrument for the collection of data, for example, if the computational system 300 is integrated into the instrument.

The data store 314 includes a block 334 of instructions that directs the processor 308 to calculate an index value from the alternative measurement. This may be performed as described with respect to FIG. 2.

The data store 314 includes a block 336 of instructions to direct the processor 308 to calculate a predicted molecular weight from the density and the index value. This may be performed as described with respect to FIG. 2. In some embodiments, a block 338 of instructions outputs the predicted molecular weight, for example, displaying the predicted molecular weight on one of the output devices 328.

In some embodiments, the data store 314 includes a block 340 of instructions to direct the processor 308 to perform a statistical analysis on the data to generate a correlation function, correlating molecular weight of a crude oil with density and an alternative measurement. In some embodiments, the correlation function is a quadratic equation.

EXAMPLES

Procedures for Alternate Measurements
Near Infrared (NIR) Measurements

The near infrared (NIR) measurement is performed without further sample preparation. Any near infrared instrument can be selected, so long as the path length and parameters are constant. In this experiment, the instrument was a Bruker OPTIK Gmbh, model MPA. The oil sample was transferred to sample cell and the spectra data was obtained in the wavenumber range 4,000 $cm^{-1}$ to 12,821 $cm^{-1}$.

Fourier Transform Infrared (FTIR) Measurements

Direct measurement. No preparation is required. The sample just filled into the sample cell and measure. Any FTIR may be used, so long as the path length and parameters are constant. In this experiment, the instrument used for the analysis of the crude oil was a Varian 660-IR (FTIR) spectrophotometer equipped with a Golden Gate ATR (attenuated total reflectance) accessory from Specac, with a diamond crystal. The background FTIR run was taken against a clean accessory. For sample analysis, three drops of crude oil were placed on the diamond crystal and the crystal was covered with a plastic cap to minimize sample evaporation. The instrument was then scanned over the wavenumber range from 4000-700 $cm^{-1}$.

Ultraviolet/Visible (UV/VIS) Measurements

Dilute solutions were prepared by dissolving the oil in a two-part solvent system consisting of iso-octane (90 mL) and dichloromethane (10 mL). In a typical solution preparation, one drop (about 6 mg+/−3 mg) of crude oil from a pre-weighed syringe is added to 100 mL of the solvent solution. The syringe is reweighed to determine the exact amount of the crude oil added. Each crude oil sample is analyzed at two concentration levels, e.g., 60 mg/L and 120 mg/L. Solutions were analyzed in 1 cm quartz cells using a Jasco V-530 double beam spectrophotometer.

Simulated Distillation (SIMDIST) Measurements

Samples were measured using SimDist without further preparation. The technique and equipment were as described with respect to ASTM D2887. In this experiment, the ASTM D2887 was performed on an Agilent 6890N (G1540N) GC. The column was DB-2887 (length 10 m, diameter 0.530 mm, film thickness 3 μm). The following GC conditions were maintained: carrier gas: helium, carrier gas flow rate: 12 mL/min, initial column temperature: 35° C., final column temperature: 350° C., programming rate: 20° C./min, Detector: FID, Detector temperature: 370° C., Injector temperature: 350° C., and sample size 0.1 μL.

Thermogravimetric Analysis (TGA) Measurements

In the experiments, TGA was conducted with TA Instruments (New Castle, Del.) Model #2050, equipped with the company's Universal Analyst and Thermal Advantage software. A sample of 15-25 mg is placed via a pipette in a commercial platinum sample pan. No sample dilution or special sample preparation is required. TGA is conducted under a nitrogen atmosphere from ambient temperature to 600° C. at 10° C./minute and a gas flow of 90+/−5 ml/min through the furnace using calibrated rotameters. A continuous flow of nitrogen (10+/−1 ml/min) through the balance chamber is also maintained.

Example 1—Data Generation

Ten crude oils were used to generate data from alternative measurements, such as spectroscopic, chromatographic and thermogravimetric data. The densities of the 10 crude oils were also measured to develop a predictive correlation using an index value calculated from the alternative measurements with the density, to predict the molecular weights of the crude oils.

A test sample of Arabian medium crude with a density of 0.8828 Kg/l (measured at 15° C. using the method described in ASTM D4052-18a, Feb. 7, 2019) was analyzed by gel permeation chromatography to determine the molecular weights using polystyrene standards. ASTM D4052 was performed on DMA 48, Anton Paar. The following conditions were maintained. The temperature for the measurement was set at 15.6° C. The cell is rinsed with a cleaning solvent and dried with acetone prior analysis. Calibration was done using air and water at the set temperature (15.6° C.): prior to calibration, the cell is rinsed with a cleaning solvent and dried. Manual injection of 1-2 mL of sample into the dry cell. Absence of gas bubbles is verified using optical method (no light). Instrument is maintained away from direct sunlight (to avoid bubbling). Instrument is maintained at low temperature and humidity environment to avoid condensation. The sample preparation and GPC conditions are summarized in Table 3.

TABLE 3

| Sample concentration and GPC conditions. | |
|---|---|
| Sample concentration | $1/100^{th}$ dilution in cyclohexane and filtered by syringe filter |
| Flow rate | 0.8 mL/min |
| Detector | UV detector at 254 nm |
| Injection volume | 2 μL |
| Run time | 15 minutes |
| Mobile phase | Dichloromethane |
| Column | Knauer Eurospher II 100-5 NH2 (250 × 8 mm, 5 μm) |
| Column oven temperature | 30° C. |

The index value was then calculated using the techniques described with respect to the method 200 of FIG. 2. The density and index values were used in the Molecular Weight equation described with respect to FIG. 2:

$$\text{Molecular Weight} = \text{Constant} + X_1 * \text{DEN} + X_2 * \text{DEN}^2 + X_3 * \text{DEN}^3 + X_4 * \text{Index} + X_5 * \text{Index}^2 + X_6 * \text{Index}^3 + X_7 * \text{DEN} * \text{Index},$$

wherein $X_1$, $X_2$, $X_3$, $X_4$, $X_5$, $X_6$, and $X_7$ are coefficients determined by a multiple regression analysis, DEN is the density value, and Index is the index value. The number of datasets depends on the number of variables. For example, at least the same number of data sets as the number of variables. One additional data set will be needed for variability. As the number of datasets is increased the error is decreased.

Example 2

TABLE 4

| Property | NIR | FTIR | UVVIS | SIMDIST | TGA |
|---|---|---|---|---|---|
| Calculations for each method (Equations) | | | | | |
| Constant | −1.6873826E+07 | 2.8832921E+06 | −3.0810862E+06 | 1.2917656E+09 | −7.7748997E+03 |
| X1 * | 56479650.5665257 * | −10133830.4104256 * | 10300857.587589 * | 308018811.431012 * | 40503.7759547847 * |
| DEN | 0.8828 | 0.8828 | 0.8828 | 0.8828 | 0.8828 |
| X2 * | −62645386.2165583* | 11767749.2647062 * | −11355273.0428965 * | −346687762.198284 * | 0 * 0.8828^2 |
| DEN^2 | 0.8828^2 | 0.8828^2 | 0.8828^2 | 0.8828^2 | |
| X3 * | 23021451.7593591 * | −4514501.98948184 * | 4133811.15621215 * | 133210335.759252 * | −28390.3361146662 * |
| DEN^3 | 0.8828^3 | 0.8828^3 | 0.8828^3 | 0.8828^3 | 0.8828^3 |
| X4 * | −361881.361442933 * | 9178.44708441325 * | −109887.636682694 * | −15146559.9142106 * | −144.713253368455 * |
| INDX | 0.7576 | 13.861945 | 0.9497 | 272.2 | 372.836 |
| X5 * | 66769.3368054301 * | −120.606405392425 * | 45920.8342306251 * | 55381.1280515201 * | 0.28341049823638 * |

TABLE 4-continued

| Property | NIR | FTIR | UVVIS | SIMDIST | TGA |
|---|---|---|---|---|---|
| INDX^2 | 0.7576^2 | 13.861945^2 | 0.9497^2 | 272.2^2 | 372.836^2 |
| X6 * INDX^3 | −38744.686878144 * 0.7576^3 | 6.70009318157926 * 13.861945^3 | −20502.4448018877 * 0.9497^3 | −67.3926609734194 * 272.2^3 | −0.00029541070899097 * 1 372.836^3 |
| X7 * DEN*INDX | 374187.845206216 * 0.8828 * 0.7576 | −10071.5160337651 * 0.8828 * 13.861945 | 88770.41002205 * 0.8828 * 0.9497 | −26706.2541091863 * 0.8828 * 272.2 | 67.7624545764978 * 0.8828 * 372.836 |
| MW Estimated | −16873825.98914265 6479650.5665257 * 0.8828-62645386.2165583 * 0.8828^2 23021451.7593591 * 0.8828^3-361881.361442933 * 0.757666769.33680 54301 * 0.7576^2 374187.845206216 * 0.8828 * 0.7576 | 2883292.06677215-10133830.4104256 * 0.882811767749.264 7062 * 0.8828^2-4514501.98948184 * 0.8828^3 9178.44708 441325 * 13.861945-120.606405392425 * 13.861945^2-10071.5160337651 * 0.8828 * 13.861945 | −3081086.1939529103 00857.587589 * 0.8828-11355273.0428965 * 0.8828^2 4133811.156 21215 * 0.8828^3-109887.636682694 * 0.949745920.8342306 251 * 0.9497^2 88770.41002 205 * 0.8828 * 0.9497 | 1291765564.576273 08018811.431012 * 0.8828-346687762.198284 * 0.8828^2 133210335.759252 * 0.8828^3-15146559.9142106 * 272.255381.1280515 201 * 272.2^2-26706.2541091863 * 0.8828 * 272.2 | −7774.8997146851140 503.7759547847 * 0.88280 * 0.8828^2-28390.3361146662 * 0.8828^3-144.713253368455 * 372.8360.2834104982 3638 * 372.836^267.7624545 764978 * 0.8828 * 372.836 |
| MW Actual | 860.00 | 860.00 | 860.00 | 860.00 | 860.00 |
| AAD | [MW estimated-MW Actual]/MW estimated *100 | [MW estimated-MW Actual]/MW estimated *100 | [MW estimated-MW Actual]/MW estimated * 100 | [MW estimated-MW Actual]/MW estimated * 100 | [MW estimated-MW Actual]/MW estimated *100 |
| Constants and values | | | | | |
| R2 | 9.7365043E−01 | 9.9902438E−01 | 9.7743810E−01 | 8.2674249E−01 | 9.9081082E−01 |
| Constant | −1.6873826E+07 | 2.8832921E+06 | −3.0810862E+06 | 1.2917656E+09 | −7.7748997E+03 |
| X1 | 5.6479651E+07 | −1.0133830E+07 | 1.0300858E+07 | 3.0801881E+08 | 4.0503776E+04 |
| X2 | −6.2645386E+07 | 1.1767749E+07 | −1.1355273E+07 | −3.4668776E+08 | 0.0000000E+00 |
| X3 | 2.3021452E+07 | −4.5145020E+06 | 4.1338112E+06 | 1.3321034E+08 | −2.8390336E+04 |
| X4 | −3.6188136E+05 | 9.1784471E+03 | −1.0988764E+05 | −1.5146560E+07 | −1.4471325E+02 |
| X5 | 6.6769337E+04 | −1.2060641E+02 | 4.5920834E+04 | 5.5381128E+04 | 2.8341050E−01 |
| X6 | −3.8744687E+04 | 6.7000932E+00 | −2.0502445E+04 | −6.7392661E+01 | −2.9541071E−04 |
| X7 | 3.7418785E+05 | −1.0071516E+04 | 8.8770410E+04 | −2.6706254E+04 | 6.7762455E+01 |
| DEN | 0.8828 | 0.8828 | 0.8828 | 0.8828 | 0.8828 |
| DEN^2 | 0.77933584 | 0.77933584 | 0.77933584 | 0.77933584 | 0.77933584 |
| DEN^3 | 0.68799768 | 0.68799768 | 0.68799768 | 0.68799768 | 0.68799768 |
| INDX | 0.758 | 13.862 | 0.9497 | 272.200 | 372.836 |
| INDX^2 | 0.57395776 | 192.1535192 | 0.90193009 | 74092.84 | 139006.6829 |
| INDX^3 | 0.434830399 | 2663.621514 | 0.856563006 | 20168071.05 | 51826695.62 |
| DEN*INDX | 0.66880928 | 12.23732505 | 0.83839516 | 240.29816 | 329.1396208 |
| Constant | −1.6873826E+07 | 2.8832921E+06 | −3.0810862E+06 | 1.2917656E+09 | −7.7748997E+03 |
| X1 * DEN | 4.9860236E+07 | −8.9461455E+06 | 9.0935971E+06 | 2.7191901E+08 | 3.5756733E+04 |
| X2 * DEN^2 | −4.8821795E+07 | 9.1710288E+06 | −8.8495713E+06 | −2.7018620E+08 | 0.0000000E+00 |
| X3 * DEN^3 | 1.5838705E+07 | −3.1059669E+06 | 2.8440525E+06 | 9.1648402E+07 | −1.9532485E+04 |
| X4 * INDX | −2.7416132E+05 | 1.2723113E+05 | −1.0436029E+05 | −4.1228936E+09 | −5.3954311E+04 |
| X5 * INDX^2 | 3.8322779E+04 | −2.3174945E+04 | 4.1417382E+04 | 4.1033451E+09 | 3.9395953E+04 |
| X6 * INDX^3 | −1.6847368E+04 | 1.7846512E+04 | −1.7561636E+04 | −1.3591800E+09 | −1.5310161E+04 |
| X7 * DEN*INDX | 2.5026030E+05 | −1.2324842E+05 | 7.4424682E+04 | −6.4174637E+06 | 2.2303309E+04 |
| MW Estimated | 894.63 | 862.73 | 912.25 | 787.58 | 884.14 |
| MW Actual | 860.00 | 860.00 | 860.00 | 860.00 | 860.00 |
| AAD | 4.03 | 0.32 | 6.08 | 8.42 | 2.81 |

Embodiments

An embodiment described in examples herein provide a method for predicting a molecular weight of a hydrocarbon fluid. The method includes measuring a density of the hydrocarbon fluid, obtaining an alternative measurement of a physical property of the hydrocarbon fluid, calculating an index value for the hydrocarbon fluid from the alternative measurement, and calculating a predicted molecular weight using an equation that combines the density with the index value. The predicted molecular weight is provided as an output.

In an aspect, the method includes obtaining the index value by measuring a near infrared (NIR) spectrum of the hydrocarbon fluid and determining the index value for the hydrocarbon fluid based, at least in part, on the NIR spectrum. In an aspect, the method includes determining the index value (NIRA) from the equation:

$$NIRA = \sum_{i=4,000}^{12,821} (Absorbance_{(i)})/10,000,$$

wherein absorbance is the absorbance value of the hydrocarbon fluid at each wavenumber (cm$^{-1}$) between 4,000 cm$^{-1}$ to 12,821 cm$^{-1}$.

In an aspect, the method includes obtaining the index value by measuring a Fourier transform infrared (FTIR) spectrum of the hydrocarbon fluid and determining the index value for the hydrocarbon fluid based, at least in part, on the FTIR spectrum. In an aspect, the method includes determining the index value (FTIRI) from the equation:

$$FTIRI = \text{maxtrans}_{desired\ crude} - \text{maxtrans}_{lowest\ value},$$

wherein the maximum transmittances (maxtrans) are determined for each of a number of hydrocarbon fluids under investigation.

In an aspect, the method includes obtaining the index value by measuring an ultraviolet/visible (UV/VIS) spectrum of the hydrocarbon fluid and determining the index value for the hydrocarbon fluid based, at least in part, on the UV/VIS spectrum. In an aspect, the method includes determining the index value (CUVISI) from the equation:

$$CUVISI = \sum_{220}^{400} 2(Absorbance/x),$$

wherein Absorbance is the absorbance value of the hydrocarbon fluid at each specific wavelength over a range of 220 nm to 400 nm at 2 nm intervals, and x is the weight of the sample used.

In an aspect, the method includes obtaining the index value by performing a simulated distillation (SIMDIST) of the hydrocarbon fluid and determining the index value for the hydrocarbon fluid based, at least in part, on the results of the SIMDIST. In an aspect, the method includes determining the index value (WABT) from the equation:

$$WABT = \frac{[T10*10 + T30*30 + T50*50 + T70*70 + T90*90]}{[10 + 30 + 50 + 70 + 90]}.$$

In an aspect, the method includes obtaining the alternative measurement by performing a thermogravimetric analysis (TGA) of the hydrocarbon fluid. In an aspect, the method includes determining the index value (TGAI) from the equation:

$$TGAI = \frac{\begin{array}{c}[5*T_5 + 10*T_{10} + 20*T_{20} + 30*T_{30} + \\ 40*T_{40} + 50*T_{50} + 60*T_{60} + \\ 70*T_{70} + 80*T_{80} + 90*T_{90} + 95*T_{95}]\end{array}}{[5+10+20+30+40+50+60+70+80+90+95]},$$

wherein $T_n$ is a temperature at each individual mass percentage.

In an aspect, the equation to calculate the predicted molecular weight is:

Molecular Weight=Constant+$X_1$*DEN+$X_2$*DEN$^2$+ $X_3$*DEN$^3$+$X_4$*Index+$X_5$*Index$^2$+$X_6$*Index$^3$+ $X_7$*DEN*Index, wherein $X_1$, $X_2$, $X_3$, $X_4$, $X_5$, $X_6$, and $X_7$ are coefficients determined by a multiple regression analysis, DEN is the density value, and Index is the index value.

Another embodiment described in examples herein provides a system for predicting a molecular weight of a hydrocarbon fluid. The system includes a processor and a data store, the data store includes code that, when executed, directs the processor to collect a density measurement, collect data from an alternative measurement, calculate an index value from the data from the alternative measurement, calculate a predicted molecular weight from the density measurement and the index value, and output the predicted molecular weight.

In an aspect, the system includes a network interface controller to access a crude oil property database, a density database, or a data collection system, or any combinations thereof. In an aspect, the system includes an input device to enter the density measurement.

In an aspect, the system includes an output device to output the predicted molecular weight. In an aspect, the output device includes a monitor.

In an aspect, the code to collect the density measurement includes a prompt for a user to enter the density measurement.

In an aspect, the code to collect the data from the alternative measurement includes operating software for an instrument collecting the data. In an aspect, the alternative measurement includes a near infrared spectrum, a Fourier transform infrared spectrum, an ultraviolet/visible spectrum, a simulated distillation, a thermogravimetric analysis, a gas chromatography measurement, a liquid chromatography measurement, or any combinations thereof.

Other implementations are also within the scope of the following claims.

What is claimed is:

1. A method for estimating a molecular weight of a hydrocarbon fluid, comprising:
    measuring a density of the hydrocarbon fluid;
    obtaining a near infrared (NIR) spectrum of the hydrocarbon fluid;
    calculating an index value (NIRA) for the hydrocarbon fluid from the NIR spectrum, wherein the NIRA is calculated from the equation:

$$NIRA = \sum_{i=4,000}^{12,821} (Absorbance_{(i)})/10,000,$$

wherein absorbance is an absorbance value of the hydrocarbon fluid at each wavenumber (cm$^{-1}$) between 4,000 cm$^{-1}$ to 12,821 cm$^{-1}$;

calculating an estimated molecular weight from the equation:

Molecular Weight=Constant+$X_1$*DEN+$X_2$*DEN$^2$+$X_3$*DEN$^3$+$X_4$*Index+$X_5$*Index$^2$+$X_6$*Index$^3$+$X_7$*DEN*Index, wherein $X_1$, $X_2$, $X_3$, $X_4$, $X_5$, $X_6$, and $X_7$ are coefficients determined by a statistical analysis correlating molecular weight of the hydrocarbon fluid with density and NIR spectrum, Constant is a constant determined by the statistical analysis, DEN is the density value, and Index is the index value; and providing the estimated molecular weight as an output.

2. The method of claim 1, wherein:
Constant is $-1.6873826*10^7$;
$X_1$ is $5.6479651*10^7$;
$X_2$ is $-6.2645386*10^7$;
$X_3$ is $2.3021452*10^7$;
$X_4$ is $-3.6188136*10^5$;
$X_5$ is $6.6769337*10^4$;
$X_6$ is $-3.8744687*10^4$; and
$X_7$ is $3.7418785*10^5$.

3. A system for estimating a molecular weight of a hydrocarbon fluid, comprising:
the hydrocarbon fluid;
a processor;
a near infrared (NIR) spectrophotometer;
a data store, comprising code that, when executed, directs the processor to:
collect a density measurement of the hydrocarbon fluid, wherein collecting the density measurement comprises prompting a user to enter the density measurement;
collect a near infrared spectrum of the hydrocarbon fluid from the spectrophotometer;
calculate an index value (NIRA) for the hydrocarbon fluid, wherein the NIRA is calculated from the equation:

$$NIRA = \sum_{i=4,000}^{12,821} (Absorbance_{(i)})/10,000,$$

wherein absorbance is an absorbance value of the hydrocarbon fluid at each wavenumber (cm$^{-1}$) between 4,000 cm$^{-1}$ to 12,821 cm$^{-1}$;

calculate an estimated molecular weight from the equation:

Molecular Weight=Constant+$X_1$*DEN+$X_2$*DEN$^2$+$X_3$*DEN$^3$+$X_4$*Index+$X_5$*Index$^2$+$X_6$*Index$^3$+$X_7$*DEN*Index, wherein $X_1$, $X_2$, $X_3$, $X_4$, $X_5$, $X_6$, and $X_7$ are coefficients determined by a statistical analysis correlating molecular weight of the hydrocarbon fluid with density and NIR spectrum, Constant is a constant determined by the statistical analysis, DEN is the density value, and Index is the index value; and output the estimated molecular weight.

4. The system of claim 3, comprising a network interface controller to access a crude oil property database, a density database, or a data collection system, or any combinations thereof.

5. The system of claim 3, comprising an input device to enter the density measurement.

6. The system of claim 3, comprising an output device to output the predicted molecular weight.

7. The system of claim 6, wherein the output device comprises a monitor.

* * * * *